United States Patent [19]
Kanno et al.

[11] Patent Number: 5,804,006
[45] Date of Patent: Sep. 8, 1998

[54] METHOD FOR JUDGING THE PROPERTIES OF MOLTEN CAST IRON

[75] Inventors: Toshitake Kanno; Jun Iwahashi; Eiichi Sahara; Hidetaka Hiraoka; Mayuki Morinaka; Tsuneharu Sugie; Yasushi Kubota, all of Shizuoka-ken, Japan

[73] Assignees: Kimura Foundry Co., Ltd.; Nippon Sublance Probe Engineering Ltd., both of Japan

[21] Appl. No.: 643,076

[22] Filed: Apr. 30, 1996

[30] Foreign Application Priority Data

May 16, 1995 [JP] Japan .................................. 7-140099

[51] Int. Cl.$^6$ ........................................................ C21D 1/54
[52] U.S. Cl. ................................ 148/511; 266/99; 75/380
[58] Field of Search ...................................... 148/508, 511; 266/99; 164/4.1; 75/377, 382, 384, 380

[56] References Cited

U.S. PATENT DOCUMENTS

| 5,057,149 | 10/1991 | Conti et al. | 75/377 |
| 5,337,799 | 8/1994 | Backerud | 75/377 |
| 5,373,888 | 12/1994 | Backerud | 164/4.1 |

*Primary Examiner*—Scott Kastler
*Attorney, Agent, or Firm*—Bierman, Muserlian and Lucas LLP

[57] ABSTRACT

A method for judging the properties of molten cast iron which consists of connecting three sampling vessels with an apparatus for obtaining a cooling curve of molten cast iron, measuring a cementite eutectic temperature (TEC) of cast iron poured to the first sampling vessel to which a chilling agent is contained, measuring a eutectic freezing temperature change of molten cast iron poured to the second sampling vessel being free of any additive, measuring a graphite eutectic temperature (TEG) of molten cast iron poured to the third sampling vessel, and inspecting a relation between the cementite eutectic temperature (TEC) and the graphite eutectic temperature (TEG) within the range of the eutectic freezing temperature change of molten cast iron.

6 Claims, 6 Drawing Sheets

5,804,006

METHOD FOR JUDGING THE PROPERTIES OF MOLTEN CAST IRON

FIELD OF THE INVENTION

This invention relates to a method for judging the properties of molten cast iron, and more particularly to a method for judging the properties of cast iron prior to casting.

PRIOR ART

The properties of cast iron cannot be determined by measuring the chemical composition thereof, and since cast iron is formed from graphite and steel, the distribution and shape of graphite in cast iron, graphitization and others must be studied, carefully.

In the prior art, in order to determine the distribution of graphite in cast iron and others, after molten cast iron has been sufficiently cooled to change the solid state, the solidified cast iron is observed under a microscope or ultrasonic apparatus to judge the properties of cast iron.

Usually, on the other hand, a chill test is carried out in pouring molten cast iron into a mold in order to confirm whether a thin portion or corner of the molding is converted into white cast iron or not.

It is confirmed that in an iron-carbon equilibrium diagram, a graphite eutectic temperature (stabilized eutectic temperature) is 1153° C. and a cementite eutectic temperature is 1147° C. Each of these temperatures, however, shows an ideal one, but these temperatures are not used for judging the properties of cast iron melt.

It is already well-known in the art that these eutectic temperatures are changed by silicon and chromium (Cr) contents in cast iron. If the silicon content in cast iron is increased, a graphite eutectic temperature will be increased and a cementite eutectic temperature will be decreased, and on the other hand, if the chromium content in cast iron is increased, the cementite eutectic temperature will be increased.

Then, in measuring a cooling curve of molten cast iron, we have studied to judge the properties of cast iron according to the eutectic, graphite eutectic and cementite eutectic temperatures of molten cast iron.

In the prior art, there is a method for determining properties of cast iron by using a cooling curve thereof in which tellurium (Te) is added to molten cast iron so as to solidify it in the form of cementite eutectic transformation, and carbon (C) and silicon (Si) contents in cast iron by using a cooling curve of molten cast iron are respectively measured from the cooling curve of cementite eutectic transformation.

According to the above method, in the case where all of chemical components in molten cast iron other than carbon and silicon including trace elements have not been changed, the carbon and silicon contents in molten cast iron may be obtained from the method for measuring the cementite eutectic temperature thereof. If the chemical components in molten cast iron, however, are slightly changed, it is very difficult to judge the carbon and silicon contents, because the cementite eutectic temperature will be changed together with the change of the components in molten cast iron.

In the method for measuring the cementite eutectic temperature of molten cast iron, a carbon equivalent (CE=C+⅓ Si) is obtained from a primary crystal temperature thereof, and then the silicon content is obtained from the cementite eutectic temperature, and therefore, it is impossible to analyze manganese (Mn) content in molten cast iron.

Since the properties of cast iron depend on the components and the rate of the cooling, even if the components are the same, the number of eutectic cell, shrinkage, strength and hardness of cast iron are usually measured by several tests after molten cast iron has been freezed.

In view of the foregoing, it is a principal object of the invention to provide a method for judging the properties of molten cast iron prior to pour it into a mold.

It is a further object of the invention to provide a method for judging the properties of molten cast iron by considering the change of a cementite eutectic temperature, graphite eutectic temperature and eutectic freezing temperature of molten cast iron.

According to the invention, the method for judging the properties of molten cast iron consists of using three sampling vessels for carrying out thermal analysis of molten cast iron, adding additive for promoting chill to the first sampling vessel and pouring molten cast iron into the first sampling vessel for measuring cementite eutectic temperature (TEC), measuring eutectic freezing temperature of molten cast iron poured into the second sampling vessel without adding no additive thereto, measuring graphite eutectic temperature (TEG) of molten cast iron poured into the third sampling vessel into which graphitizer is added, and inspecting the relation between the above cementite eutectic temperature (TEC) and the graphite eutectic temperature (TEG) with respect to the change of the above eutectic temperature of the molten cast iron.

According to the invention, about 0.2 to 1.0% by weight of tellurium (Te) is out in the first sampling vessel as the additive for promoting chilling effect. It is possible to substitute selenium (Se), bismuth (Bi) and chromium (Cr) for about 50% by weight of tellurium to be added.

In this instance, if the content of silicon in the molten cast iron is less than 30% by weight, the ability of graphitization will substantially be decreased. On the other hand, if the content of silicon in molten cast iron is larger than 97% by weight, the ability of graphitization will be decreased. Although carbon is effective substance for graphitization of molten cast iron, if the content of carbon is less than 30% by weight, the ability of graphitization will be decreased.

BRIEF DESCRIPTION OF THE DRAWINGS

The invention is illustrated by way of example in the accompanying drawings which form part of this application in which.

DETAILED DESCRIPTION

The invention will now be explained in more detail with reference to the drawings.

Figure 1:
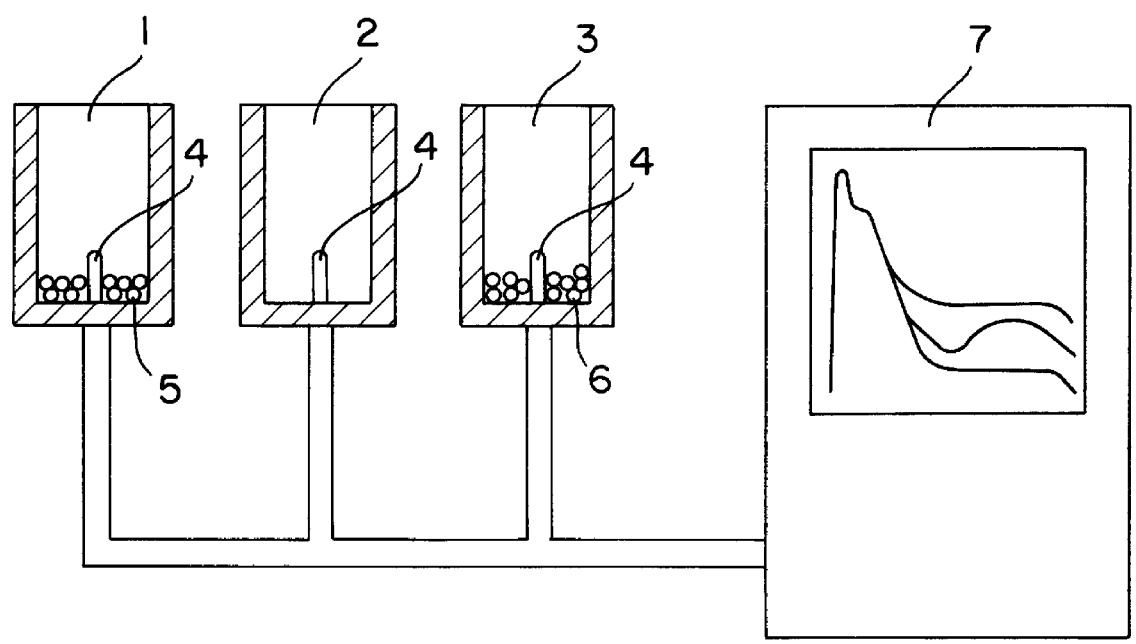
FIG. 1 shows a schematic illustration of three sampling vessels and apparatus for plotting a cooling curve carrying out the invention.

As shown in FIG. 1, three sampling vessels, that is, the first, second and third vessels 1, 2 and 3 having a conventional thermocouple 4 are respectively connected with a cooling curve recorder 7 such as a conventional CE meter.

As one of the structure modifying additives, a small quantity of tellurium (Te) is placed in the first vessel 1, but the second vessel 2 is free of the additive and 75% by weight of ferosilicon 6 is placed in the third vessel 3.

The following five samples of the molten cast iron comprising carbon (C), silicon (Si), magnesium (Mn) and chromium (cr) were prepared:

Sample I: 3.1% of carbon (C), 1.6% of silicon (Si), 0.75% of manganese (Mn) and 0.12% of chromium (Cr);

Sample II: 3.1% of C, 1.6% of Si, 0.75% of Mn and 0.37% of Cr;

Sample III: 3.1% of C, 1.6% of Si, 0.75% of Mn and 0.63% of Cr;

Sample IV: 3.1% of C, 1.6% of Si, 0.75% of Mn and 0.91% Cr; and

Sample V: 3.1% of C, 1.6% of Si, 0.75% of Mn and 1.38% of Cr.

By using a conventional CE meter and the sampling vessels 1, 2 and 3 and the apparatus 7 of the invention, the fading of each of the samples I–V is measured and the relation between the chill depth and the cooling curve of each of the samples are respectively investigated.

Figure 2:
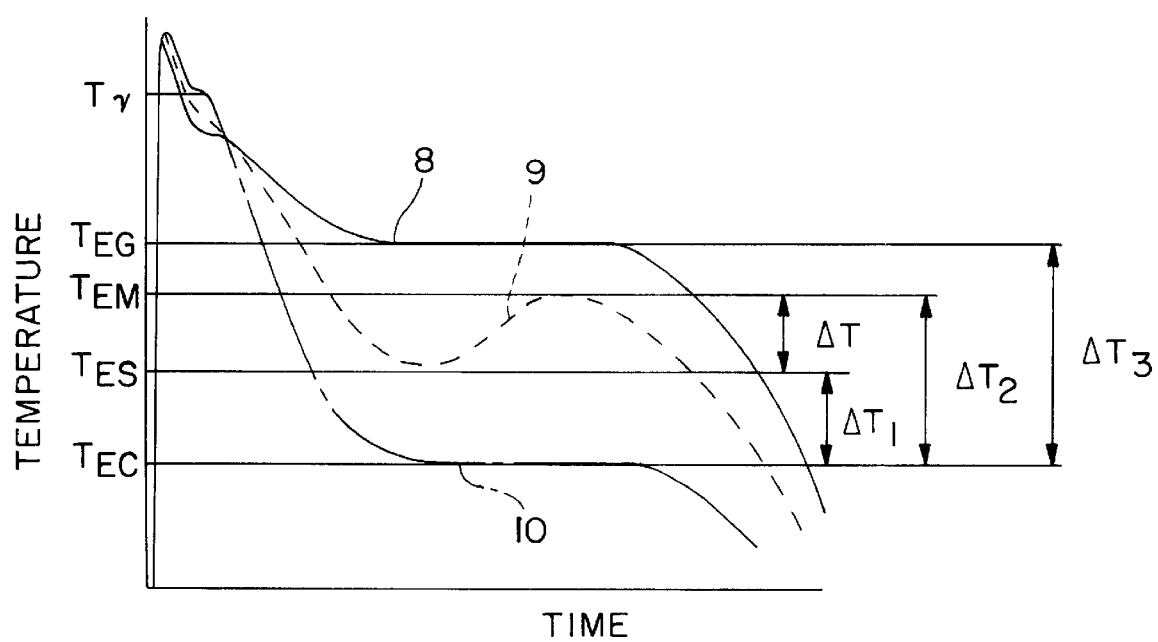
FIG. 2 is a diagram explaining a cooling curve of molten cast iron obtained from the sampling vessels and apparatus shown in FIG. 1.

The cooling curve obtained from the samples poured in the second sampling vessel 2 in which no additive is contained is shown as a broken line 9 in FIG. 2.

In this cooling curve 9, the temperature difference (ΔT) between the highest eutectic freezing temperature (TEM) and the lowest eutectic supercooling temperature (TES) of molten cast iron is a conventional one and usually, it is considered that this temperature difference (ΔT) is related to the chill depth.

Figure 3:
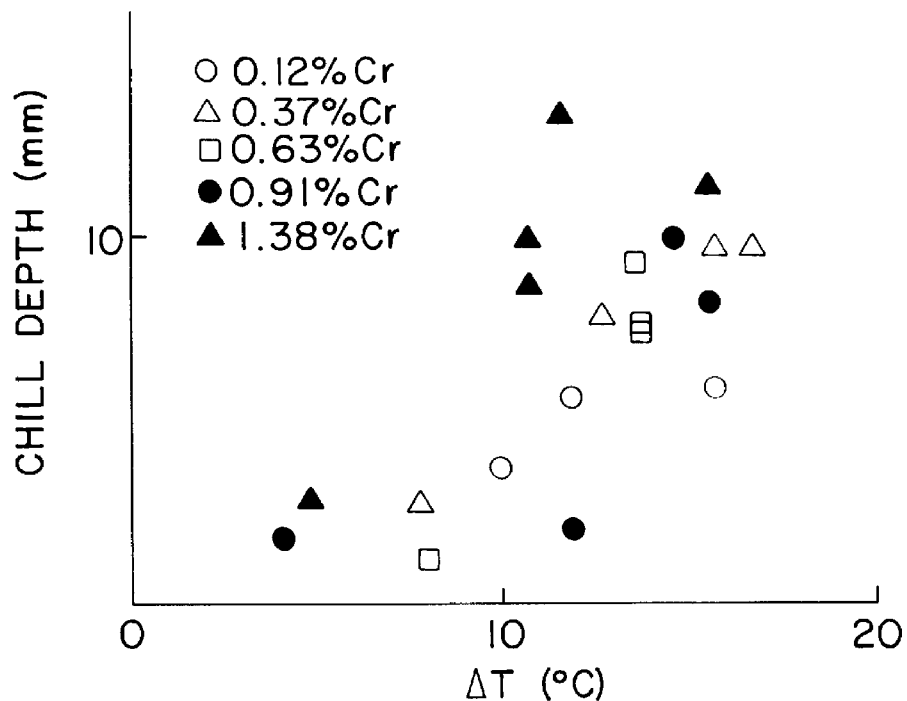
FIG. 3 is a diagram showing a relation of a temperature difference ($\Delta T$) between the highest eutectic temperature (TEM) and the lowest eutectic supercooling temperature (TES) owing to variation of the content of chromium (Cr) in molten cast iron and the chill depth.

According to the cooling curve 9 shown in FIG. 2, the temperature difference (ΔT) between the highest eutectic freezing temperature (TEM) and the lowest eutectic supercooling temperature (TES) of each of the samples I–V may be plotted as shown in FIG. 3. From FIG. 3 it will be recognized that there is no relation between the temperature difference (ΔT) and the chill depth.

A cooling curve 10 in FIG. 2 shows the cementite eutectic temperature (TEC) obtained from the melt of cast iron poured into the first sampling vessel 1 in which tellurium (Te) is contained.

In FIG. 2 the temperature difference between the lowest eutectic supercooling temperature (TES) in the cooling curve 8 and the cementite eutectic temperature (TEC) in the cooling curve 10 is denoted by ΔT1.

Figure 4:
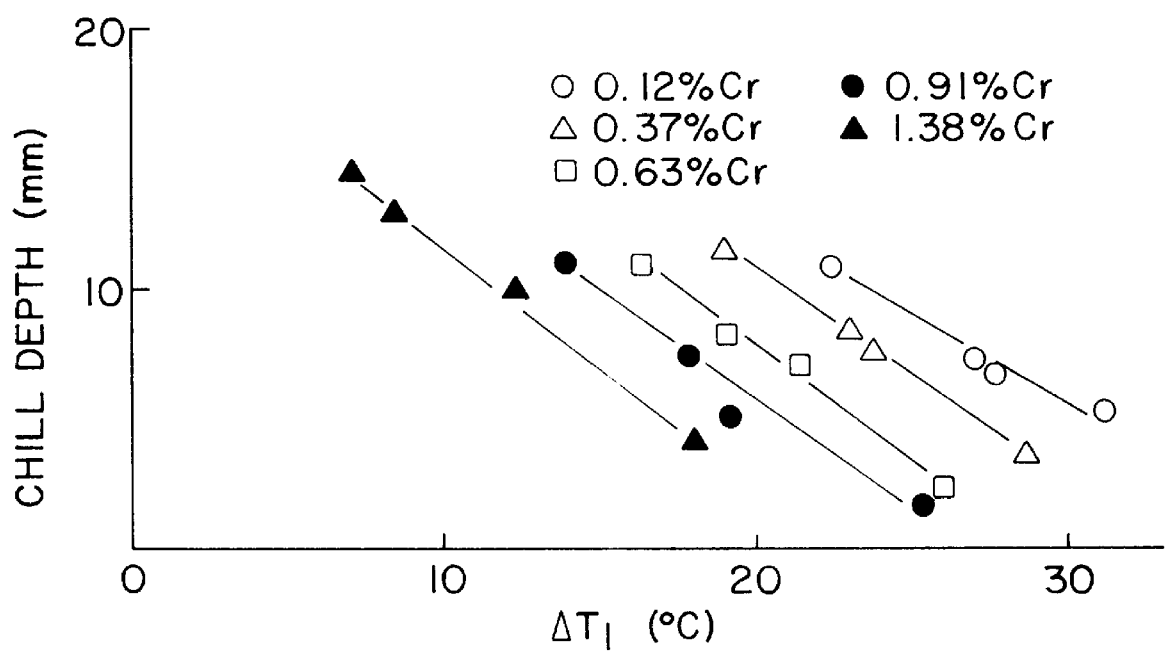
FIG. 4 is a diagram showing a relation of a temperature difference ($\Delta T$) between the lowest supercooling eutectic temperature (TES) and the cementite eutectic temperature (TEC) owing to variation of the content of chromium (Cr) in molten cast iron and the chill depth.

The temperature difference (ΔT1) and the chill depth of each of the samples I–V may be plotted as shown in FIG. 4.

From FIG. 4, it will be appreciated that when the content of chromium in each of the samples is in an equal amount, the temperature difference (ΔT1) between the lowest eutectic supercooling temperature (TES) has a good relation with the chill depth, but if the content of chromium in molten cast iron is changed, the relation between the temperature difference (T1) and the chill depth will be deteriorated.

Further, from the cooling curves obtained from the sampling vessels 1, 2 and 3, it will be recognized that according to the relation between the temperature difference (ΔT3) between the graphite eutectic temperature (TEG) and the cementite eutectic temperature (TEC) and the temperature difference (ΔT1) between the lowest eutectic supercooling temperature (TES) and the cementite eutectic temperature (TEG) (ΔT1/ΔT3) values have a closed relation with each other.

Figure 5:
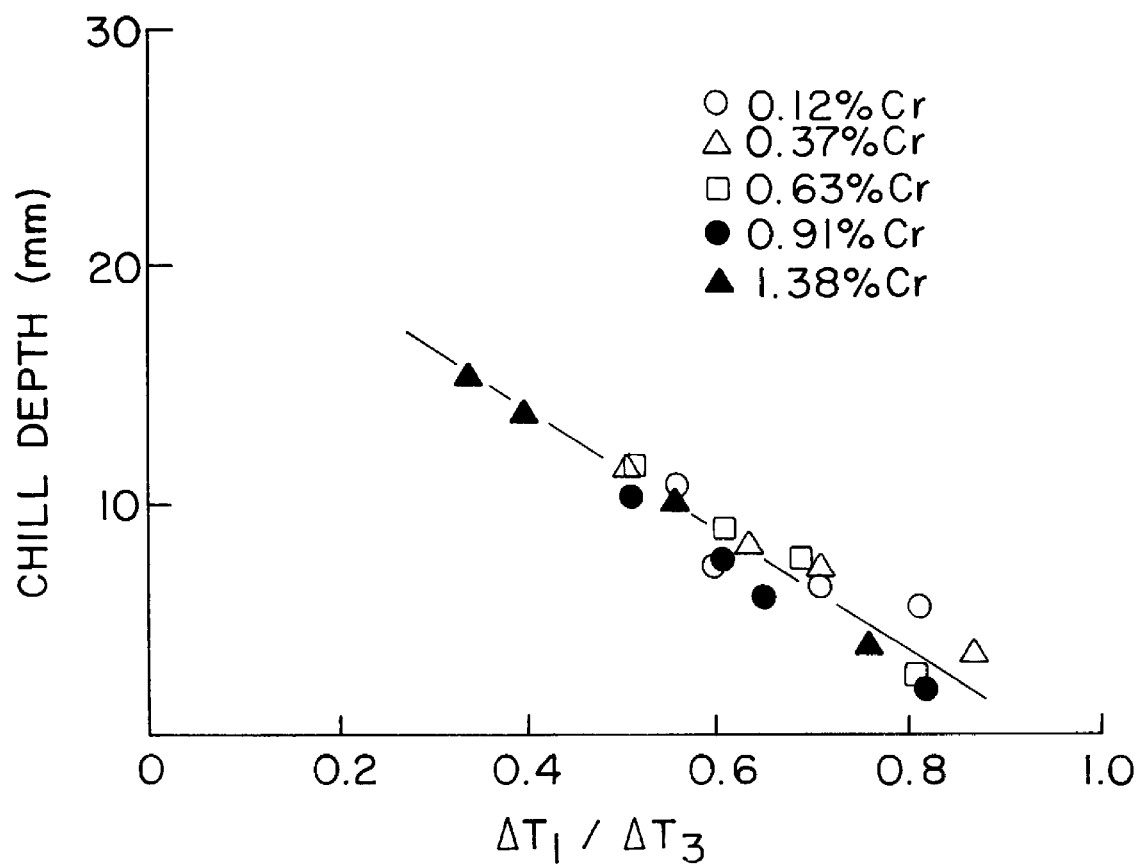
FIG. 5 is a diagram showing a relation of $\Delta T1/T3$ owing to variation of chromium in molten cast iron and the chill depth.

FIG. 5 shows a relation between the chill depth obtained by using a chill test piece and (ΔT1/ΔT3) values.

If the content of chromium in the molten cast iron is changed, the relation between the temperature difference (ΔT1) between the lowest eutectic supercooling temperature (TES) and the cementite eutectic temperature (TEC) and the chill depth will not be in good condition, but by using the above relation (ΔT1/ΔT3), the relation between it and the chill depth will be improved.

As a result of investigating the structure of cast iron obtained from the third sampling vessel 3 in which 75% ferrosilicon is contained, all the type of graphite is in A type.

Figure 6:
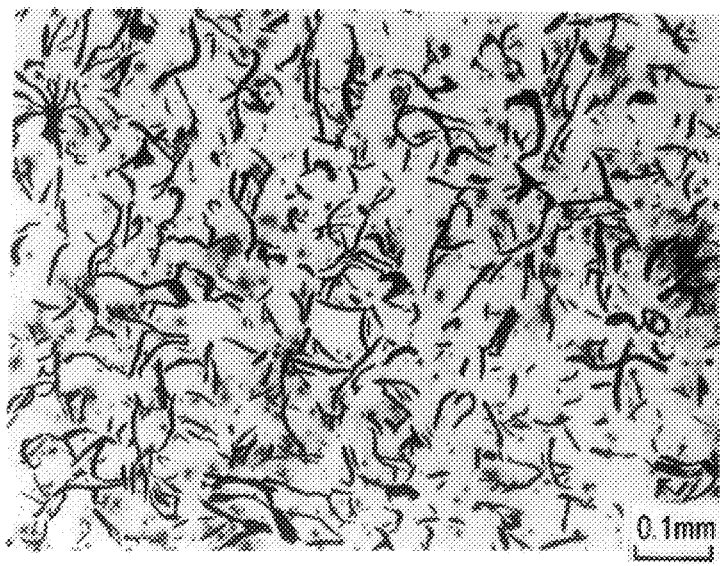
FIG. 6 is a photomicrograph showing the cast iron structure formed from molten cast iron having $\Delta T1/\Delta T3$ value of 0.73 which is poured into the second sampling vessel to which no additive is introduced.
Figure 7:
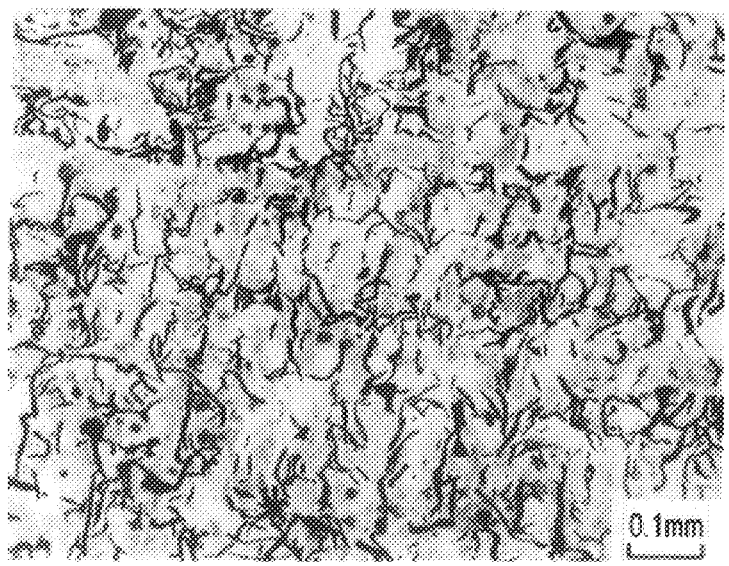
FIG. 7 is a photomicrograph showing the cast iron structure formed from molten cast iron having ΔT1/ΔT3 value of 0.56 which is poured into the second sampling vessel to which no additive is introduced.
Figure 8:
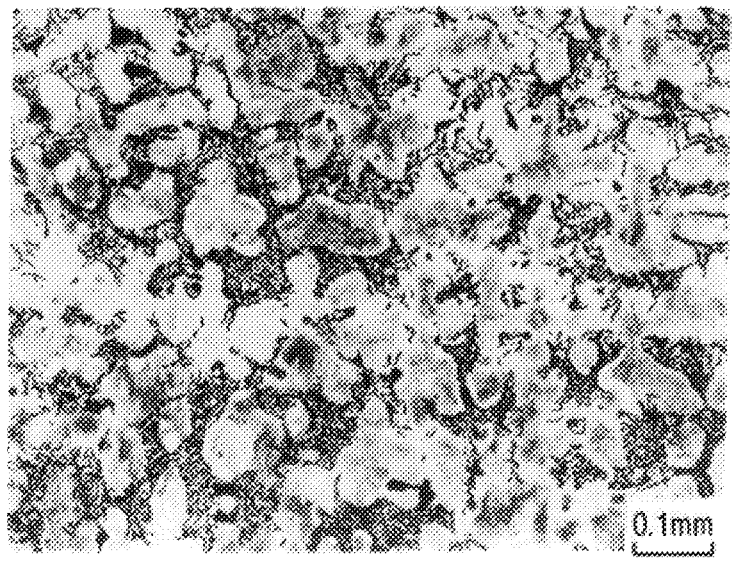
FIG. 8 is a photomicrograph showing the cast iron structure formed from molten cast iron having ΔT1/ΔT3 value of 0.25 which is poured into the second sampling vessel to which no additive is introduced.

Accordingly, as shown in FIGS. 6, 7 and 8, it will be recognized that there is significant relation among ΔT1/ΔT3 values, the types of graphite and the distribution of graphite in cast iron.

Figure 9:
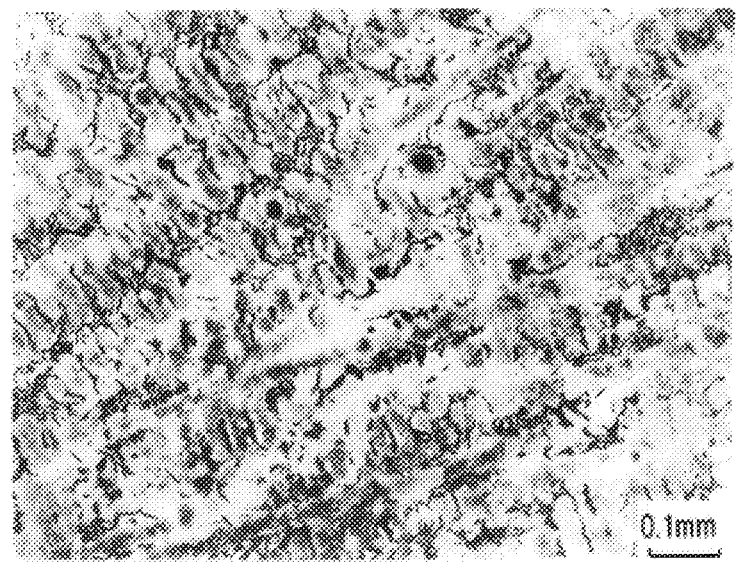
FIG. 9 is a photomicrograph showing the cast iron structure formed from molten cast iron having ΔT1/ΔT3 value of 0.10 which is poured into the second sampling vessel to which no additive is introduced.

In the drawings illustrating microstructure of cast iron, FIG. 6 shows the structure having ΔT1/ΔT3 value of 0.73, and FIG. 7 shows the structure having T1/T3 value of 0.56, FIG. 8 shows the structure having ΔT1/ΔT3 value of 0.25 and FIG. 9 shows the structure having ΔT1/ΔT3 value of 0.10, respectively.

The properties of these structures, time of fading, ΔT1/ΔT3 value, type of graphite, strength, hardness, shrinkage, content of carbide and number of eutectic cell are shown in Table I.

TABLE I

| Fading (minute) | ΔT1/ΔT3 | Type of Graphite | Strength (N/mm2) | Hardness (HB) | Shrinkage | Carbide (%) | Number of Eutectic Cells (/cm2) |
|---|---|---|---|---|---|---|---|
| 0 | 0.73 | A | 311 | 201 | Yes | 0 | 145 |
| 5 | 0.56 | E | 290 | 201 | No | 0 | 125 |
| 15 | 0.25 | D | 248 | 223 | No | 0.1 | 95 |
| 25 | 0.10 | D | 277 | 235 | No | 1.2 | 81 |

From the microstructure shown in FIGS. 6 to 9, it will be able to understand that if ΔT1/ΔT3 values are closer to 1, granite distributed in cast iron will be in A type, and on the other hand, if ΔT1/ΔT3 values are closer to 0, graphite is not distributed uniformly in cast iron.

Further, it is apparent from FIGS. 6 to 9 and the above table I that if the type of graphite decreases, strength of cast iron, and the numbers of eutectic cell therein will be decreased.

In the case where ΔT1/T3 value is 0.25, the hardness of cast iron will be increased for the reason that small quantity of carbide is formed therein, and in the case where T1/T3 value is 0.10, the existence of carbide in the structure is confirmed.

From the foregoing, it is found that ΔT1/ΔT3 value and the number of eutectic cell are closely related to each other.

In consequence of the above, even if ΔT1/ΔT3 values are selected by using the temperature difference (ΔT2) between the highest eutectic freezing temperature (TEM) and the cementite eutectic temperature (TEC), it is not necessary to consider the relation between the two as far as the highest eutectic freezing temperature is not the same as the graphite eutectic temperature (TEG). The position of the highest eutectic freezing temperature TEM) in between the cementite eutectic temperature (TEC) and the graphite eutectic temperature (TEG) may be depicted by the area in the side of the cementite eutectic temperature (TEC) and the area in the side of the graphite eutectic temperature (TEG).

Furthermore, it is possible to judge the properties of the molten cast iron by examining the primary crystallization temperature (Tr), carbon equivalent, the temperature difference (ΔT) between the highest eutectic temperature (TEM) and the lowest eutectic supercooling temperature (TES), and the relation between the temperature and time in the eutectic freezing of molten cast iron.

As stated in the foregoing, the properties of the molten cast iron may be judged prior to pouring it into a mold in the foundry test.

What we claim is:

1. A method for judging the properties of molten cast iron, comprising:
   (a) measuring a cementite eutectic temperature (TEC) of molten cast iron poured into a first sampling vessel in which chilling agent is contained;
   (b) measure an eutectic freezing temperature of molten cast iron poured to a second sampling vessel free of any additive;
   (c) measuring a graphite eutectic temperature (TEG) of molten cast iron poured to a third sampling vessel into which griphatizer is contained; and
   (d) determining the temperature difference (DT) between the cementite eutectic temperature (TEC) and the graphite eutectic temperature (TEG) within the range of the eutectic freezing temperature change of molten cast iron to determine the properties of the cast iron melt.

2. A method as claimed in claim 1 wherein molten cast iron is poured into each of the first, second and third sampling vessels, simultaneously.

3. A method as claimed in claim 1 wherein the chilling agent is selected from the group consisting of tellurium, selenium, bismuth and chromium.

4. A method as claimed in claim 2 wherein the chilling agent is at least one member of the group consisting of tellurium, selenium, bismuth and chromium.

5. A method as claimed in claim 1 wherein graphitizer contains about 30 to 97% by weight of silicon.

6. A method as claimed in claim 1 wherein graphitizer contains about 30% by weight of carbon.

* * * * *